United States Patent
Lantermann et al.

(10) Patent No.: US 10,258,422 B2
(45) Date of Patent: Apr. 16, 2019

(54) INSTRUMENT HOLDER FOR SURGICAL END EFFECTORS AND METHOD FOR ARRANGING AN INSTRUMENT HOLDER

(71) Applicant: Deutsches Zentrum Fuer Luft-Und Raumfahrt E.V., Cologne (DE)

(72) Inventors: Sophie Lantermann, Munich (DE); Michael Strohmayer, Augsburg (DE)

(73) Assignee: DEUTSCHES ZENTRUM FUER LUFT-UND RAUMFAHRT E.V., Cologne (DE)

( * ) Notice: Subject to any disclaimer, the term of this patent is extended or adjusted under 35 U.S.C. 154(b) by 410 days.

(21) Appl. No.: 14/891,122

(22) PCT Filed: Mar. 12, 2014

(86) PCT No.: PCT/EP2014/059669
§ 371 (c)(1),
(2) Date: Nov. 13, 2015

(87) PCT Pub. No.: WO2014/184148
PCT Pub. Date: Nov. 20, 2014

(65) Prior Publication Data
US 2016/0081750 A1 Mar. 24, 2016

(30) Foreign Application Priority Data
May 17, 2013 (DE) .......... 10 2013 209 211

(51) Int. Cl.
*A61B 50/20* (2016.01)
*A61B 50/22* (2016.01)
(Continued)

(52) U.S. Cl.
CPC .......... *A61B 50/20* (2016.02); *A61B 19/0256* (2013.01); *A61B 19/54* (2013.01);
(Continued)

(58) Field of Classification Search
CPC ......... A61B 50/20; A61B 50/22; A61B 90/98; A61B 17/04
(Continued)

(56) References Cited

U.S. PATENT DOCUMENTS 3,696,920 A 10/1972 Lahay
5,411,059 A 5/1995 Sever et al.
(Continued)

FOREIGN PATENT DOCUMENTS

| JP | 2008284255 A | 11/2008 |
|---|---|---|
| WO | 2004019803 A1 | 3/2004 |
| WO | 2012142442 A2 | 10/2012 |

OTHER PUBLICATIONS

International Search Report dated Aug. 19, 2014 for PCT application No. PCT/EP2014/059669.
(Continued)

*Primary Examiner* — Aaron F Roane
(74) *Attorney, Agent, or Firm* — Ohlandt, Greeley, Ruggiero & Perle, LLP

(57) ABSTRACT

To arrange surgical end effectors used in minimally invasive surgery, the disclosure provides an instrument holder which can be arranged inside the body of the patient. An instrument holder of this kind has a base part having multiple receptacles. The volume of the base part can be varied for the purpose of inserting the base part into the human body, and removing it therefrom, by way of a trocar. A method is also provided for arranging an instrument holder for surgical end effectors used in minimally invasive surgery inside the patient body.

17 Claims, 1 Drawing Sheet

(51) Int. Cl.
*A61B 19/02* (2006.01)
*A61B 19/00* (2006.01)
*A61B 90/98* (2016.01)
*A61B 17/00* (2006.01)
*A61B 90/00* (2016.01)

(52) U.S. Cl.
CPC .............. *A61B 50/22* (2016.02); *A61B 90/98* (2016.02); *A61B 2017/00283* (2013.01); *A61B 2017/00353* (2013.01); *A61B 2017/00362* (2013.01); *A61B 2017/00473* (2013.01); *A61B 2017/00557* (2013.01); *A61B 2019/0258* (2013.01); *A61B 2090/0804* (2016.02)

(58) Field of Classification Search
USPC ..................................................... 606/1, 148
See application file for complete search history.

(56) References Cited

U.S. PATENT DOCUMENTS

| | | |
|---|---|---|
| 6,309,397 B1 | 10/2001 | Julian et al. |
| 2005/0283137 A1 | 12/2005 | Doyle et al. |
| 2007/0055294 A1* | 3/2007 | Giap ................ A61B 17/06066 606/148 |
| 2009/0209947 A1 | 8/2009 | Gordin et al. |

OTHER PUBLICATIONS

Written Opinion dated Nov. 17, 2015 for corresponding International Application No. PCT/EP2014/059669.
International Preliminary Report on Patentability Opinion dated Nov. 17, 2015 for corresponding International Application No. PCT/EP2014/059669.

\* cited by examiner

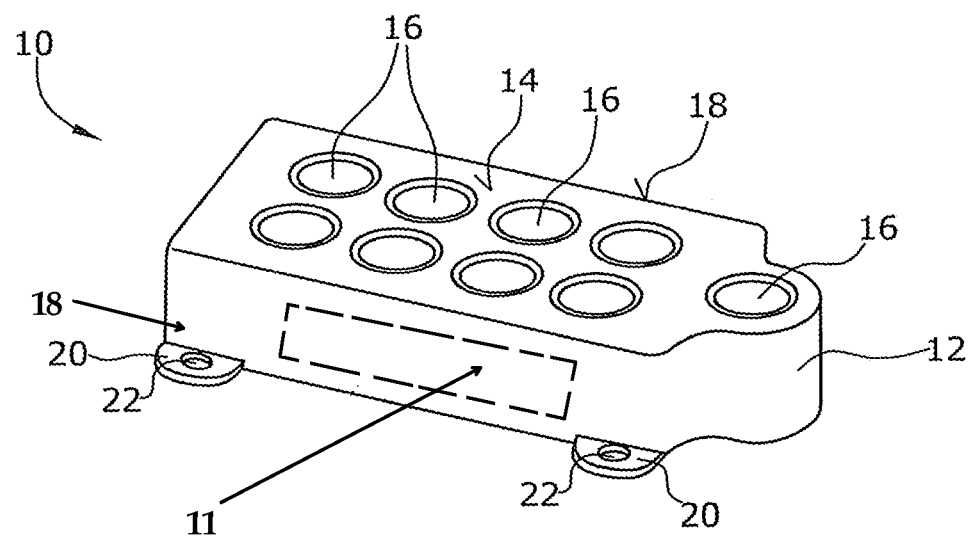

INSTRUMENT HOLDER FOR SURGICAL END EFFECTORS AND METHOD FOR ARRANGING AN INSTRUMENT HOLDER

BACKGROUND

1. Field of the Disclosure

The disclosure relates to an instrument holder for surgical end effectors, in particular for minimally invasive surgery.

2. Discussion of the Background Art

In minimally invasive surgery instruments are introduced into a patient via so-called trocars. Such an instrument has an instrument support with which an end effector, such as a surgical instrument like a forceps, a pair of scissors and the like, is connected. A surgical end effector (forceps, pair of scissors etc.) is arranged at the distal end of the instrument support. Up to now, it is necessary to exchange the entire instrument during an operation. This is performed manually by an assistant surgeon or a surgical nurse on request of a surgeon. For an exchange of an instrument it is therefore required to withdraw the instrument from the patient through the trocar and to perform the corresponding manual exchange of the instrument. This is time consuming and thus extends the duration of an operation. This not only results in higher costs, but also in greater stress for the patient, in particular because of the longer periods of narcosis. A further problem is that a contamination of the instrument may occur during the exchange of the instrument. This may lead to infections prolonging the healing process.

An instrument holder for surgical end effectors is known from U.S. Pat. No. 3,696,920, which is suited for use in minimally invasive surgery. The instrument holder is adapted to receive a plurality of surgical end effectors. It is thus possible, after having pulled the instrument holder from the patient through the trocar, to replace the current end effector with another end effector arranged in the instrument holder. To receive the end effectors, the instrument holder described in U.S. Pat. No. 3,696,920 is made from semirigid foam. Thereby, the necessary holding forces for the end effector are generated.

It is an object of the disclosure to provide an instrument holder for surgical end effectors, in particular for minimally invasive surgery, which allows for a simpler exchange of the end effector.

Further, it is an object of the disclosure to provide a method for arranging an instrument holder, in particular for minimally invasive surgery, which allows for a simpler exchange of the end effector.

SUMMARY

The instrument holder for surgical end effectors of the present disclosure comprises a plurality of receptacles for different surgical end effectors. The receptacles are arranged in a base part. According to the disclosure the volume of the base part is variable. In particular, the volume of the base part may be reduced. Inside the patient, the volume of the base part is enlarged again so that the same is suited to receive different surgical end effectors. Due to the provision of an instrument holder in the abdomen, the exchange of end effectors may be performed near the site of operation. In particular an automatic exchange of end effectors is possible so that it is no longer necessary to pull the entire instrument from the trocar and to manually exchange the entire instrument. This results in a substantial saving of time and a reduction in costs and in stress for the patient. Further, the risk of an infection of the patient is significantly reduced.

According to the disclosure the variation of the base part volume may be realized in different ways. It is preferred, for example, that the base part comprises a compressible material or is made entirely of a compressible material. This may be a suitable polymer, for example. To introduce the base part into the body of a patient, the base part may thus be compressed and may be introduced into the interior of the body with the help of a suitable end effector connected with the instrument holder. In case of an elastically deformable base part, the same will automatically restore its original shape as soon as no more pressing or compression is exerted. In this original shape, the receptacles are designed in a corresponding manner, so that different surgical end effectors may be set into the receptacles.

In a further embodiment of the disclosure the base part is, at least in part, preferably elastically deformable and/or foldable and/or rollable.

In another preferred embodiment the base part has a fluid chamber. The same may be filled or emptied so that the volume of the base part can thereby be varied in a simple manner. Filling may be realized using a gas and/or a liquid.

The receptacles provided in the base part may differ in design. In particular, they are plug-in openings into which the individual surgical effectors needed during an operation may be inserted or from which they may be pulled out. It is preferred that the receptacles comprise holding elements for holding the surgical end effectors. In this regard it is possible that, owing to the deformability of the base part, the end effectors are retained in the receptacles by friction and/or by locking elements, bayonet joints, threads or the like.

In a further preferred embodiment the base part comprises fixing elements. By means of the fixing elements, such as fixing tabs, for example, it is possible to fix the instrument holder in the body, e.g. by suturing. Fixing may also be achieved by reversible adhesive bonding, by vacuum mechanisms and the like.

In a further preferred embodiment the instrument holder comprises an active and/or passive marker element. This may be a RFID tag, for example. Using sensors provided on corresponding trocars, for example, it is thus possible to ensure that the instrument holder will be removed from the interior of the body.

BRIEF DESCRIPTION OF THE DRAWINGS

The FIGURE illustrates a schematic perspective view of a preferred embodiment of an instrument holder.

DETAILED DESCRIPTION OF THE PREFERRED EMBODIMENT

According to the disclosure, to exchange a surgical end effector, which is connected with an instrument holder, during operation, the instrument holder is first arranged at the operation site in order to provide the surgical end effectors. This is done by inserting the instrument holder, which is reduced in volume, through a trocar. Within the operation site, the volume of the base part is increased again, e.g. by unfolding, rolling out, inflating or the like. This may also happen in a self-acting manner, if the base part is a body of elastically deformable material. In the next step, the instrument holder is fastened in the body e.g. by suturing, reversible adhesive bonding or by vacuum mechanisms.

In the next step, the instrument holder is equipped with the surgical end effectors necessary for the operation. Here, the individual end effectors may be connected with the distal end of the instrument holder via e.g. a bayonet joint, a locking joint or the like. The individual surgical end effectors are introduced one after the other into the body and are transferred to the instrument holder to equip the same. For this purpose, the instrument holder may also comprise a holding device for the surgical instruments, which device may be in the form of locking elements, bayonet joints or the like. Especially due to the deformability and elasticity of the base part, it is also possible that the surgical end effectors are fixed in the receptacles by the effect of friction. In this context, the individual receptacles may be designed in a manner specific to the end effectors.

During an operation, it is thus made possible in a simple manner to exchange the surgical end effectors at the distal end of the instrument holder, without having to pull the same from the body, by transferring individual end effectors to the instrument support and by receiving a new end effector.

Preferably, documentation is provided in order to ensure that at the end of an operation neither an end effector, nor the instrument holder remain in the patient's body. In this regard, each individual end effector and the instrument holder may for example be provided with sensors, so that the surgical end effectors introduced into the body are detected. Since the end effectors are pulled out of the body one by one using the instrument holder, it is also possible to document which end effector has been removed from the body. Corresponding sensors could also be provided on the instrument holder, in particular on the base part of the instrument holder, so that also the removal of the instrument holder is ensured.

It is also possible to provide sensors on the trocar, for example, which detect the surgical end effectors and the instrument holder introduced into or removed from the body.

The instrument holder is removed from the body cavity by first removing the instrument holder from a body wall, whereafter the base part is deformed or compressed and the compressed base part is then removed from the body cavity through the trocar.

A surgical instrument system for minimally invasive surgery thus comprises an instrument holder, a plurality of surgical end effectors and an instrument support. Further, a trocar may be provided, with at least the trocar, the instrument holder and possibly also the surgical end effectors themselves being provided with sensors.

The disclosure further relates to a method for arranging an instrument holder for surgical end effectors. According to the disclosure, the instrument holder which is designed and developed in particular as described above, is arranged inside the patient, i.e. inside the abdomen. In this regard, it is possible to reduce the volume of the base part of the instrument holder which comprises a plurality of receptacles for receiving the end effectors. The reduction in volume allows the instrument holder to be introduced into the interior of a patient via a trocar, i.e. a small opening. After insertion of the instrument holder into the interior of a patient, the volume of the base part of the instrument holder is enlarged again, so that the same can receive end effectors while inside the patient. In a further step, the instrument holder is fixed e.g. by being sutured in the interior of a patient.

The base part 10 is reduced in volume in particular by compressing and/or folding and/or rolling up the base part 10. Accordingly, the volume of the base part 10 is enlarged inside the patient by decompressing and/or unfolding and/or rolling out the base part. In a particularly preferred embodiment the base part 10 has a fluid chamber 11. By fluid discharge, i.e. in particular by drawing off a fluid such as air from the fluid chamber 11, the volume of the base part 10 is reduced to the required size so as to allow the same to be inserted into the interior of the patient through the trocar. By supplying fluid into the fluid chamber 11, the base part 10 is enlarged again inside the patient.

The method of the present disclosure is developed in particular as described above with reference to the instrument holder itself.

An instrument holder of the present disclosure will be described in detail hereinbelow with reference to the accompanying drawing.

As shown in the FIGURE, the instrument holder has a base part 10 which in the embodiment illustrated is substantially of parallelepiped shape having a protrusion 12 substantially in the shape of a cylindrical segment of a circle. In a top side 14 of the instrument holder a plurality of openings 16 are provided which, in the embodiment illustrated, are cylindrical. The openings 16 form the receptacles into which the surgical end effectors can be inserted. While being held available, the surgical end effectors are fixed in the receptacles 16 by friction or retaining elements such as bayonet joints, locking elements or the like.

At a side wall 18, fixing elements 20 are provided in the lower part of the base part 10. Correspondingly, two fixing elements 20 are also provided on the opposite side 18. In the embodiment illustrated the fixing elements 20 are formed as fixing tabs so that the instrument holder can be sutured in the patient body via openings 22 provided in the fixing elements.

What is claimed is:

1. An instrument holder for surgical end effectors for minimally invasive surgery, comprising:
   a base part with a plurality of receptacles for receiving surgical end effectors,
   wherein the base part has a volume that is reducible for the purpose of introducing the base part into an interior of a patient via a trocar, and
   wherein the base part has a fluid chamber for the purpose of varying the volume.

2. The instrument holder of claim 1, wherein the base part comprises a compressible material to allow for a variation of the volume.

3. The instrument holder of claim 1, wherein the base part is at least partly deformable to allow for a reduction in volume.

4. The instrument holder of claim 1, wherein the base part is at least partly foldable to allow for a reduction in volume.

5. The instrument holder of claim 1, wherein the base part is at least partly adapted to be rolled up/out to allow for a variation in volume.

6. The instrument holder of claim 1, wherein the plurality of receptacles are configured as plug-in openings in the base part.

7. The instrument holder of claim 1, wherein the base part is connected with fixing elements.

8. The instrument holder of claim 7, wherein the fixing elements are fixing tabs.

9. A method for arranging an instrument holder for surgical end effectors for minimally invasive surgery according to claim 1, said method comprising the following:
   reducing the volume of the base part with the plurality of receptacles, such that the base part may be inserted through the trocar of the patient, inserting the base part into the interior of the patient via the trocar, and increasing the volume of the base part within the patient so that the base part is suited for receiving surgical instruments.

10. The method of claim 9, wherein the reduction in volume is achieved by compressing the base part.

11. The method of claim 9, wherein the reduction in volume of the base part is achieved by folding.

12. The method of claim 9, wherein the reduction in volume of the base part is achieved by rolling up.

13. The method of claim 9, wherein the base part comprises the fluid chamber, with fluid being discharged in order to reduce the volume.

14. The method of claim 9, wherein the base part is fixed inside the patient.

15. The method of claim 14, wherein the base part is fixed inside the patient by suturing to the interior of the patient.

16. An instrument holder for surgical end effectors for minimally invasive surgery, comprising:

a base part with a plurality of receptacles for receiving surgical end effectors, wherein base part has a volume that is reducible for the purpose of introducing the base part into an interior of a patient via a trocar, wherein the base part is connected with fixing elements, and wherein the fixing elements are fixing tabs.

17. An instrument holder for surgical end effectors for minimally invasive surgery, comprising:

a base part with a plurality of receptacles for receiving surgical end effectors, wherein base part has a volume that is reducible for the purpose of introducing the base part into an interior of a patient via a trocar, and wherein the base part comprises an active or a passive marker element.

* * * * *